(12) United States Patent
Hagemeyer et al.

(10) Patent No.: US 9,073,036 B2
(45) Date of Patent: Jul. 7, 2015

(54) CATALYST FOR THE OXIDATION OF HYDROCARBONS CONSISTING OF MOLYBDENUM, VANADIUM, NIOBIUM, TELLURIUM, MANGANESE AND COBALT

(75) Inventors: Alfred Hagemeyer, Sunnyvale, CA (US); Gerhard Mestl, Munich (DE); Silvia Neumann, Grosskarolinenfeld (DE); Andras Tompos, Tata (HU); Jozsef Margitfalvi, Budapest (HU); Lajos Istvan Vegvari, Kismaros (HU)

(73) Assignee: Clariant Produkte (Deutschland) GmbH, Frankfurt am Main (DE)

( * ) Notice: Subject to any disclaimer, the term of this patent is extended or adjusted under 35 U.S.C. 154(b) by 0 days.

(21) Appl. No.: 14/237,621

(22) PCT Filed: Aug. 9, 2012

(86) PCT No.: PCT/EP2012/065616
§ 371 (c)(1),
(2), (4) Date: May 9, 2014

(87) PCT Pub. No.: WO2013/021034
PCT Pub. Date: Feb. 14, 2013

(65) Prior Publication Data
US 2014/0336411 A1 Nov. 13, 2014

(30) Foreign Application Priority Data

Aug. 9, 2011 (DE) .......................... 10 2011 109 816

(51) Int. Cl.
| | | |
|---|---|---|
| *C07C 51/16* | (2006.01) | |
| *B01J 37/04* | (2006.01) | |
| *B01J 27/057* | (2006.01) | |
| *B01J 37/03* | (2006.01) | |
| *B01J 37/08* | (2006.01) | |
| *B01J 23/889* | (2006.01) | |
| *B01J 35/00* | (2006.01) | |
| *B01J 35/10* | (2006.01) | |
| *B01J 37/00* | (2006.01) | |
| *B01J 37/02* | (2006.01) | |
| *C07C 51/25* | (2006.01) | |

(52) U.S. Cl.
CPC ............ *B01J 27/0576* (2013.01); *B01J 37/033* (2013.01); *B01J 37/036* (2013.01); *B01J 37/04* (2013.01); *B01J 37/08* (2013.01); *B01J 37/084* (2013.01); *B01J 23/8898* (2013.01); *B01J 35/002* (2013.01); *B01J 35/1009* (2013.01); *B01J 35/1014* (2013.01); *B01J 37/0009* (2013.01); *B01J 37/0215* (2013.01); *C07C 51/252* (2013.01); *B01J 2523/00* (2013.01); *C07C 51/16* (2013.01)

(58) Field of Classification Search
CPC .... C07C 51/252; C07C 57/04; B01J 27/0576; B01J 37/036; B01J 37/0215; B01J 37/033; B01J 37/08; B01J 37/0009; B01J 37/084; B01J 37/04; B01J 23/8898; B01J 35/1014; B01J 35/1009; B01J 35/002; B01J 2523/00
USPC .......................................... 562/549; 502/312
See application file for complete search history.

(56) References Cited

U.S. PATENT DOCUMENTS

| | | | |
|---|---|---|---|
| 6,166,241 A * | 12/2000 | Kayou et al. .................. 558/318 |
| 8,222,461 B2 | 7/2012 | Fischer et al. |
| 2003/0017944 A1 | 1/2003 | Hinago et al. |
| 2004/0063990 A1 | 4/2004 | Gaffney et al. |
| 2005/0054880 A1 | 3/2005 | Dubois et al. |
| 2006/0004228 A1 | 1/2006 | Hazin |

FOREIGN PATENT DOCUMENTS

| | | |
|---|---|---|
| DE | 101 45 958 A1 | 5/2002 |
| DE | 10 2009 054 229 A1 | 7/2011 |
| EP | 0 970 942 A1 | 1/2000 |
| EP | 1 574 254 A2 | 9/2005 |
| JP | 07-053448 | 2/1995 |
| WF | WO 03/045886 A2 | 6/2003 |
| WO | WO 2004/033090 A1 | 4/2004 |
| WO | WO 2008/046843 A1 | 4/2008 |

OTHER PUBLICATIONS

T. Ushikubo, et al., "Ammoxidation of Propane over Mo—V—Nb—Te Mixed Oxide Catalysts," Studies in Surface Science and Catalysis 112, (1997), pp. 473-480.
P. De Santo et al., "Structural aspects of the M1 and M2 phases in MoVNbTeO propane ammoxidation catalysts," Z. Kristallogr. 219 (2004) pp. 152-165.
H. Hibst et al., "New Cs-containing Mo—V4+ based oxides with the structure of the M1 phase-Base for new catalysts for the direct alkane activation," Science Direct Catalysis Today 2006, 117, pp. 234-241.
Brunauer et al., "Adsorption of Gases in Multimolecular Layers," J. Am. Chem. Soc., vol. 60, pp. 309-319 (1938).
H.M. Rietveld, "A Profile Refinement Method for Nucleear and Magetic Structures," J. Appl. Cryst., vol. 2, pp. 65-71 (1969).
International Search Report mailed Oct. 15, 2012 for International Application No. PCT/EP2012/065616.

* cited by examiner

*Primary Examiner* — Shailendra Kumar
(74) *Attorney, Agent, or Firm* — RatnerPrestia (57) ABSTRACT

A catalyst material for the oxidation and/or oxidative dehydrogenation of hydrocarbons, in particular for the selective oxidation of propane to acrylic acid, comprising a) molybdenum (Mo), b) vanadium (V), c) niobium (Nb), d) tellurium (Te), e) manganese (Mn) and cobalt, in which the molar ratio of at least one element, which is selected from manganese and cobalt, to molybdenum lies in the range 0.01 to 0.2. Furthermore, a catalyst for the oxidation and/or oxidative dehydrogenation of hydrocarbons, a use of the catalyst material or of the catalyst, a method for producing a catalyst material for the oxidation and/or oxidative dehydrogenation of hydrocarbons, and a method for the selective oxidation of propane to acrylic acid.

19 Claims, 2 Drawing Sheets

CATALYST FOR THE OXIDATION OF HYDROCARBONS CONSISTING OF MOLYBDENUM, VANADIUM, NIOBIUM, TELLURIUM, MANGANESE AND COBALT

CROSS-REFERENCE TO RELATED APPLICATIONS

This application is a U.S. National Stage application, claiming benefit under 35 U.S.C. §§120 and 365 of International Application No. PCT/EP2012/065616, filed Aug. 9, 2012, and claiming benefit under 35 U.S.C. §119 of German Application No. 10 2011 109 816.3, filed Aug. 9, 2011, the entire disclosures of both prior applications being incorporated herein by reference in their entirety.

BACKGROUND

The present invention relates to a catalyst material for the oxidation and/or oxidative dehydrogenation of hydrocarbons, a catalyst for the oxidation and/or oxidative dehydrogenation of hydrocarbons, a use of the catalyst material or of the catalyst, a method for producing a catalyst material for the oxidation and/or oxidative dehydrogenation of hydrocarbons and a method for the selective oxidation of propane to acrylic acid.

MoVNbTeO$_x$ mixed oxides for the oxidation of propane to acrylic acid are state of the art. More than 200 patents and numerous scientific publications discuss catalysts based on MoVNbTe mixed oxides. The promotion of these mixed oxides with other metals of the periodic table is known. The highest acrylic acid yields previously described are 50%.

The MoVNbTe base system, based on four elements, for a catalyst was first proposed by Mitsubishi for the ammoxidation of propane to acrylonitrile (1991) and the oxidation to acrylic acid (1994). Since then, numerous further publications have dealt with the improvement of this catalyst for example by promotion, supporting and "spiking" with noble metals.

The previously achieved yields of 50% are not sufficient for a commercialization of the process. Yields of approximately 60 to 65% acrylic acid are desired. However, such yields have not yet been achieved with multi-metal systems based on four or five elements.

Catalysts for the oxidation and/or oxidative dehydrogenation of alkanes are usually complex multi-metal oxides, based on molybdenum and vanadium oxides. As previously explained, catalysts for the selective oxidation of propane to acrylic acid are of particular interest, wherein only yields of approximately 50% acrylic acid have been achieved with mixed oxides of molybdenum, vanadium, niobium and tellurium.

MoVNbTeO$_x$ catalysts mainly consist of two orthorhombic phases, which are called "M1" and "M2" (T. Ushikubo, K. Oshima, A. Kayou, M. Hatano, Studies in Surface Science and Catalysis 112, (1997), 473). The phase M1 seems to play a part in the propane activation as an example of an oxidative dehydrogenation, while the phase M2 could be active and selective in the oxidation of propylene to acrylic acid. The M2 phase has more tellurium than the phase M1. It is assumed that Te is an active element in the propylene conversion. It is additionally assumed that Te has a stabilizing effect on the M1 phase.

According to P. De Santo et al., Z. Kristallogr. 219 (2004) 152, the main phases M1 and M2 in multi-metal oxide catalysts for the oxidation of propane can be described for example with the following structural formulae:

M1

$Mo_1V_{0.15}Te_{0.12}Nb_{0.128}O_{3.7}$ or
$Mo_{7.8}V_{1.2}Te_{0.937}Nb_1O_{28.9}$

M2

$Mo_1V_{0.32}Te_{0.42}Nb_{0.08}O_{4.6}$ or
$Mo_{4.31}V_{1.36}Te_{1.81}Nb_{0.33}O_{19.81}$

Attempts have also been made to partially replace tellurium with caesium in the M2 structure. An improved activity for the ammoxidation of propylene to acrylonitrile was observed with such a catalyst (H. Hibst, F. Rosowski, G. Cox, Catal. Today 2006, 117, 234-241).

Furthermore, as mentioned above, promotions of the MoVNbTe base system with other metals have been tested. For example, WO 2008/046843 describes mixed oxide catalysts which contain bismuth.

SUMMARY

The object of the present invention was to provide a catalyst material which promotes the yield and/or selectivity of the oxidation and/or oxidative dehydrogenation of hydrocarbons, in particular the selective oxidation of propane to acrylic acid.

This object is achieved by a catalyst material for the oxidation and/or oxidative dehydrogenation of hydrocarbons according to claim 1 or 18, a catalyst for the oxidation and/or oxidative dehydrogenation of hydrocarbons according to claim 12, a use of the catalyst material or of the catalyst according to claim 14, a method for producing a catalyst material for the oxidation and/or oxidative dehydrogenation of hydrocarbons according to claim 15 and a method for the selective oxidation of propane to acrylic acid according to claim 19.

An embodiment of the present invention relates to a catalyst material for the oxidation and/or oxidative dehydrogenation of hydrocarbons, in particular for the selective oxidation of propane to acrylic acid, comprising
 a) molybdenum (Mo)
 b) vanadium (V)
 c) niobium (Nb)
 d) tellurium (Te)
 e) manganese (Mn)
 f) cobalt (Co)
in which the molar ratio of at least one element, which is selected from manganese and cobalt, to molybdenum lies in the range of from 0.01 to 0.2, more preferably 0.02 to 0.15 and particularly preferably from 0.03:1 to 0.1:1.

In a further embodiment, a catalyst for the oxidation and/or oxidative dehydrogenation of hydrocarbons is provided comprising a catalyst material according to the above embodiment.

Another embodiment relates to a use of a catalyst material according to the first-named embodiment above or of a catalyst of the above embodiment for the oxidation and/or oxidative dehydrogenation of hydrocarbons or for the selective oxidation of propane to acrylic acid.

In a further embodiment, a method for producing a catalyst material for the oxidation and/or oxidative dehydrogenation of hydrocarbons is provided, in particular for the selective oxidation of propane to acrylic acid, comprising providing a catalyst material as catalyst precursor material according to the first-named embodiment above as aqueous mixture, and thermally treating the aqueous mixture at temperatures of from 100 to 250° C. or 150 to 200° C. for at least 1 hour and/or at a pressure in the range of from 3 to 35 bar, preferably 5 to 30 bar, more preferably 10 to 27 bar.

All non-mutually exclusive features described here of embodiments and examples can be combined with one another. Elements of one embodiment can be used in the other embodiments without further mention. Embodiments and examples of the invention are described in more detail below with reference to figures, without wishing to limit them thereby.

DETAILED DESCRIPTION

Embodiments and examples of the invention are described here with reference to a catalyst material with an MoVNbTe base system doped with manganese and cobalt, in which the molar ratio of vanadium, niobium and tellurium to molybdenum lies in the range of from approximately 0.1:1 to approximately 0.3:1 or from approximately 0.13:1 to approximately 0.27:1 and in which the molar ratio of manganese and cobalt to molybdenum lies in the range of from approximately 0.01 to 0.2, more preferably 0.02 to 0.15 and particularly preferably from 0.03:1 to approximately 0.1:1, without limiting the invention to this.

The term "hydrothermal" predominantly refers to reaction conditions for producing a catalyst material in the presence of water and at increased temperature and/or increased pressure, for example in an autoclave. In particular, the term "hydrothermal" refers to the reaction conditions of a method for producing a catalyst material by providing a catalyst precursor material as aqueous mixture, followed by thermal treatment at increased temperature, e.g. at 150 to 200° C. for at least 1 hour, without limiting the invention to this.

In embodiments, the term "comprising" includes "substantially consisting of" or "consisting of" and can be replaced by these. This applies accordingly to grammatical variants of the word "comprising". Furthermore, when value ranges are described here, the specification of a wide range with narrower alternative or preferred ranges also discloses ranges which can be formed by any combination of specified lower range limits with specified upper range limits.

In addition, in embodiments of the invention, the term "free of", for example free of particular elements of the periodic table, means substantially free of these elements. For example, the elements in question are present in the catalyst material in immeasurably small concentrations or in ranges of less than 500 ppm.

As explained above, an embodiment of the present invention relates to a catalyst material for the oxidation and/or oxidative dehydrogenation of hydrocarbons, in particular for the selective oxidation of propane to acrylic acid, comprising a) molybdenum (Mo), b) vanadium (V), c) niobium (Nb), d) tellurium (Te), e) manganese (Mn) and f) cobalt (Co), in which the molar ratio of at least one element, which is selected from manganese and cobalt, to molybdenum lies in the range of from approximately 0.01 to 0.2, more preferably 0.02 to 0.15 and particularly preferably from 0.03:1 to approximately 0.1:1. In this embodiment of the catalyst material, nickel can optionally be contained, for example in a molar ratio to molybdenum in the range of from 0 to 0.04, preferably 0.005 to 0.035. In a variant of this embodiment, the molar ratio of all elements, selected from manganese and cobalt, to molybdenum can lie in the range of from approximately 0.01 to 0.2, more preferably 0.02 to 0.15 and particularly preferably from 0.03:1 to approximately 0.1:1.

Furthermore, the molar ratio of at least one element, which is selected from vanadium, niobium and tellurium, to molybdenum can lie in the range of from approximately 0.1:1 to approximately 0.3:1 or approximately 0.13:1 to approximately 0.27:1. For example, the molar ratio of vanadium to molybdenum can lie in the range of from approximately 0.18:1 to approximately 0.28:1 and/or the molar ratio of niobium and/or tellurium to molybdenum can lie in the range of from approximately 0.13:1 to approximately 0.25:1 or 0.15:1 to approximately 0.2:1.

It has surprisingly been shown within the framework of the present invention that the use of an MoVNbTe base system, which is doped at the same time with Mn and Co and optionally with Ni, as catalyst material leads to previously unachieved yields of products of the oxidation and/or oxidative dehydrogenation of hydrocarbons, in particular in the selective oxidation of propane to acrylic acid. It was furthermore found that surprisingly high selectivities can also be achieved.

If the molar ratio of at least one element, which is selected from manganese and cobalt, to molybdenum lies in the range of from approximately 0.01 to 0.2, more preferably 0.02 to 0.15 and particularly preferably from 0.03:1 to approximately 0.1:1 and/or the molar ratio of at least one element, which is selected from vanadium, niobium and tellurium, to molybdenum lies in the range of from approximately 0.1:1 to approximately 0.3:1 or approximately 0.13:1 to approximately 0.27:1, particularly suitable yields and/or selectivities in the oxidation and/or oxidative dehydrogenation of hydrocarbons can be achieved.

The catalyst material can be used as active material or in an active material for producing catalysts.

In embodiments of the catalyst material, nickel can be contained in a molar ratio to molybdenum in the range of from 0 to 0.04.

In further embodiments, the X-ray diffractogram of the catalyst material can have diffraction reflexes h, i, k and l, the peaks of which lie approximately at the diffraction angles (2θ) 26.0±0.5 (h), 27.1±0.5 (i), 7.8±0.5 (k) and 28.0±0.5 (l). The intensities $P_h$, $P_i$, $P_k$, $P_l$ of the diffraction reflexes h, i, k and l can satisfy the following equations, with $R_{x\ (x=1\ to\ 3)}$ as the intensity ratio defined by the equations:

$$R_1 = P_h/(P_h + P_i) > 0.3\text{, preferably} > 0.33 \text{ and particularly preferably} > 0.36; \text{and/or}$$

$$R_2 = P_i/(P_i + P_l) > 0.5\text{, preferably} > 0.6 \text{ and particularly preferably} > 0.63; \text{and/or}$$

$$R_3 = P_i/(P_i + P_k) < 0.8\text{, preferably} < 0.7\text{, particularly preferably} < 0.67.$$

In the X-ray diffractogram of embodiments of the catalyst material, the diffraction reflex i can have the second highest intensity and/or the diffraction reflex h can have the third highest intensity.

In embodiments, of the diffraction reflexes h, i, k and l, the diffraction reflex i can have the highest intensity and/or the diffraction reflex h can have the second highest intensity and/or the diffraction reflex l can have the third highest intensity.

According to embodiments, the catalyst material can be a catalyst precursor material.

In embodiments, the catalyst precursor material can contain at least one excipient, with a molar ratio of at least one of the excipients to molybdenum in the range of from 0.05:1 to 0.15:1 or from 0.06:1 to 0.1:1. The at least one excipient can furthermore be selected from polyols, polyetherols, in particular ethylene glycol, propylene glycol, glycerol, butylene glycol, and/or from citric acid, tartaric acid, malic acid, lactic acid, pyruvic acid, oxalic acid, malonic acid, glycolic acid, glyoxylic acid, gluconic acid, glucuronic acid, oxamic acid, oxaloacetic acid, tricarballylic acid, glyceric acid, tartronic acid, succinic acid, glutaric acid, sorbitol, mannitol, maleic acid, fumaric acid, nitrilotriacetic acid, or any mixture thereof.

The catalyst precursor material can contain citric acid and/or ethylene glycol, with a molar ratio of citric acid and/or ethylene glycol to molybdenum in the range of from approximately 0.05:1 to approximately 0.15:1, preferably in the range of from approximately 0.06:1 to approximately 0.1:1. It can be especially preferred if citric acid and/or ethylene glycol is contained with a molar ratio to molybdenum of approximately 0.05:1, 0.075:1 or 0.1:1.

In further embodiments, the catalyst material of the above embodiments and examples can contain such quantities of vanadium, niobium, tellurium, cobalt, manganese, nickel, ethylene glycol and/or citric acid that these have approximately the following molar ratios to molybdenum:
V: 0.22 or 0.23
Nb: 0.18 or 0.195
Te: 0.18 or 0.196
Mn: 0.07 or 0.08
Co: 0.0375
Ni: 0 or 0.02
ethylene glycol: 0.075 and/or
citric acid: 0.075.

These molar ratios of the named metals to molybdenum lead to particularly suitable catalyst precursor materials or catalyst materials and thus to particularly high yields of acrylic acid and/or a particularly high selectivity in the oxidation of propane to acrylic acid.

According to embodiments, the catalyst material can be a mixed oxide and/or a multi-metal oxide.

In embodiments, the catalyst material is a mixed oxide with the formula $MoV_aNb_bTe_cMn_dCo_eNi_fO_x$ and in which at least one of the following conditions applies:
a=0.22 or 0.23
b=0.18 or 0.195
c=0.18 or 0.196
d=0.07 or 0.08
e=0.0375
f=0 or 0.02 and
x=2.635 or mole number which is determined by the valence and frequency of the elements other than oxygen.

The mixed oxide of embodiments can be obtained for example by a hydrothermal synthesis and/or after an activation and/or calcining of the above catalyst precursor material.

In embodiments of the catalyst material, in particular a catalyst material present as mixed oxide, the molar ratio of oxygen to metal lies in the range of from 2 to 3, preferably from 2.5 to 2.7. In further embodiments, the catalyst material has a reduction rate of between 2 and 3, in particular of 2.635.

For example, a thermogravimetric oxidation of a mixed oxide obtained in embodiments displays an integral weight gain of approx. 0.79 wt.-%+0.12 wt.-% after heating to 500° C. for 290 min. up to the constant weight, i.e. the weight gain is approx. 0.91 wt.-% in total. A molar ratio of oxygen to metal in the powder of the activated mixed oxide used of approximately 2.635 is calculated from the elemental composition of the metallic cations obtained by analysis of the mixed oxide of embodiments by means of ICP-AES (inductively coupled plasma atomic emission spectroscopy) and this weight gain, assuming the complete oxidation of all constituent metal ions. This results in a reduction rate of the mixed oxide of embodiments of approximately 2.635 from the weight gain, assuming the complete oxidation of all metal ions.

In a variant of the above embodiment, the catalyst material present as mixed oxide also contains carbon, which can form in the hydrothermal synthesis and/or activation and/or calcining from the above-named excipients.

Instead of or in addition to the above-mentioned citric acid and ethylene glycol, the following can be used as excipient in embodiments: polyols, polyetherols, in particular propylene glycol, glycerol, butylene glycol, and/or tartaric acid, malic acid, lactic acid, pyruvic acid, oxalic acid, malonic acid, glycolic acid, glyoxylic acid, gluconic acid, glucuronic acid, oxamic acid, oxaloacetic acid, tricarballylic acid, glyceric acid, tartronic acid, succinic acid, glutaric acid, sorbitol, mannitol, maleic acid, fumaric acid, nitrilotriacetic acid, or any mixture thereof. In these cases, the catalyst material can contain carbon as mixed oxide in small residual quantities. The quantities of carbon are negligibly small in some examples, e.g. if the material is calcined in air at ~300° C.

In variants of embodiments, the catalyst material can be free of at least one element selected from Ta, In, Cu, Ce, Cr, Bi, Fe, P, Sb, Sn, Si, Ti, Zr, W, optionally Ni, noble metals, such as Rh, Pd, Ag, Ir, Pt, Au. This leads to a particularly advantageous structure of the mixed oxide with regard to the yields of acrylic acid and/or selectivities achievable when used as catalytically active material during the oxidation of propane to acrylic acid.

The catalyst material can be obtainable or obtained hydrothermally in embodiments, for example by one of the hydrothermal syntheses described here. Alternatively or in addition, the catalyst material can be activated, for example by a thermal treatment in a stream of inert gas. Furthermore, the catalyst material can be present in powder form.

As regards the phase composition of the catalyst material, in embodiments the M1 phase can be predominantly present, relative to the catalyst material, e.g. >70 wt.-% M1, preferably >80 wt.-% M1, particularly preferably >90 wt.-% M1, wherein the remainder can consist predominantly or substantially of the M2 phase. The remainder can contain for example more than 90 wt.-%, preferably more than 95 wt.-%, more preferably more than 98 wt.-% M2 phase. In embodiments of the invention, the catalyst material can also contain phase-pure M1 or substantially consist thereof. For example, a Rietveld analysis of the X-ray diffractogram of embodiments for the catalyst material results in a proportion greater than 99 wt.-% M1, thus almost 100 wt.-% M1, with very small proportions of unknown phases, e.g. with a proportion of unknown phases lying far below 1 wt.-%.

Furthermore, in embodiments, the X-ray amorphous proportion of the catalyst material can be smaller than 40%, in particular smaller than 37%, wherein % is to be understood in each case to be vol.-%. By X-ray amorphous is meant here a material the structure of which can no longer be detected with the usual XRD (X-ray diffractometry). This can be very small ordered regions (microcrystalline) as well as statistically unordered regions. An estimation of the X-ray amorphous material proportion can be carried out by calculating the percentage proportion from the proportion of the surface area of the X-ray reflexes and the total intensity of the diffractogram, taking into account the instrumental background. This estimation follows the procedure of a Rietveld calculation (Rietveld, H. M.; A profile refinement method for molecular and magnetic structures, J. Appl. Cryst. 2 (1969) pages 65 to 71) and is based on the assumption that in an X-ray diffractogram the crystallinity of the measured material can be ascertained by determining the ratio of the intensity of the diffraction reflexes to the total intensity.

Furthermore, in embodiments the catalyst material can have a specific surface area according to BET, also called BET surface area, in the range of from 1 to 40 m²/g, preferably 3-30 m²/g, particularly preferably 5-20 m²/g. One embodiment has a BET surface area of 8.8 m²/g, another embodiment has a BET surface area of 12 m²/g.

As indicated above, the present invention also relates to a catalyst for the oxidation and/or oxidative dehydrogenation of hydrocarbons which comprises a catalyst material according to an embodiment of the present invention. The catalyst material can be applied to a support of the catalyst. For example, the pulverulent catalyst material can be applied suspended in a so-called washcoat and/or dissolved on a catalyst support, which can be formed annular, by dipping, spraying or in another way. The material of the support or catalyst support can contain for example ceramic, steatite, Duranite, silicon oxide, silicates, aluminium oxide, aluminates, silicon carbide, Raschig rings of ceramic or metal or mixtures thereof or can substantially consist thereof.

The catalyst material according to embodiments or the catalyst of embodiments can be used for the oxidation and/or oxidative dehydrogenation of hydrocarbons or for the selective oxidation of propane to acrylic acid. As explained above, yields of acrylic acid of over 50%, e.g. up to 59%, can be achieved.

The catalyst material according to the invention for the oxidation and/or oxidative dehydrogenation of hydrocarbons, in particular for the selective oxidation of propane to acrylic acid, can be produced by a method which comprises: providing a catalyst precursor material of an embodiment as aqueous mixture, and thermally treating the aqueous mixture at temperatures of from approximately 100 to 250° C. or 150 to 200° C. for at least 1 hour. Preferred temperatures are 160 to 190° C. or 170 to 180° C. The pressure can lie in the range of from 3 to 35 bar, preferably of from 5 to 30 bar. Examples of pressure ranges are 11 to 15 bar, approximately 17 bar and 22 to 25 bar.

The aqueous mixture can be produced as suspension or as solution.

The method can include one or more steps of washing, filtering, e.g. filtering off the mother liquor, drying, activating, grinding, shaping, e.g. extruding, tabletting and/or coating.

After the thermal treatment of the aqueous mixture, the thermally treated mixture can be activated e.g. in an inert gas atmosphere at approximately 500 to 700° C. for at least 1 hour. It is preferred if the thermal treatment takes place at a temperature in the range of from approximately 100 to 250° C. or approximately 150 to 200° C. and/or the activation takes place in the range of from approximately 550 to 650° C. For example, the thermal treatment can be carried out at approximately 175° C. for approximately 3 hours and/or the activation can take place at approximately 600° C. for approximately 2 hours.

One embodiment of the invention specifies a catalyst material which is obtainable or obtained by a method according to an embodiment.

The invention also relates to a method for the selective oxidation of propane to acrylic acid in the presence of oxygen and a catalyst according to the invention.

Methods

To determine the parameters of the catalysts according to the invention, the following methods are used:

1. BET Surface Area:

The determination takes place according to the BET method in accordance with DIN 66131; a publication of the BET method is also found in J. Am. Chem. Soc. 60, 309 (1938). The sample to be determined was dried in a U-shaped quartz reactor at 200° C. under Ar atmosphere (F=50 ml(min) for 1.5 h). The reactor was then cooled to room temperature, evacuated and dipped in a Dewar flask with liquid nitrogen. The nitrogen adsorption was carried out at 77 K with an RXM 100 sorption system (Advanced Scientific Design, Inc.).

The BET surface area was determined in respect of the samples of the catalyst material in each case using the uncalcined material dried under vacuum at 200° C. The data in the present description with respect to the BET surface areas of the catalyst material also relate to the BET surface areas of the catalyst material used in each case (dried under vacuum at 200° C., uncalcined).

2. Powder X-Ray Diffractometry (XRD)

The X-ray diffractogram was produced by powder X-ray diffractometry (XRD) and evaluation according to the Scherrer formula. The XRD diffractograms were measured using the catalyst materials activated at 600° C. in nitrogen. Measurement took place in a PW 1050 Bragg-Brentano parafocussing goniometer based on a Philips PW 3710 model at 40 kV and 35 mA using Cu Kα radiation (lambda=0.15418 nm), a graphite monochromator and a proportional counter. The XRD scans were recorded digitally with a step size of 0.04° (2 theta).

As already mentioned above, the estimation of the X-ray amorphous proportion of the catalyst material followed the procedure of a Rietveld calculation (Rietveld, H. M.; A profile refinement method for molecular and magnetic structures, J. Appl. Cryst. 2 (1969) pages 65 to 71) and was based on the assumption that in an X-ray diffractogram the crystallinity of the measured material can be ascertained by determining the ratio of the intensity of the diffraction reflexes to the total intensity. The instrumental background of the X-ray diffractogram was subtracted from the total intensity. The DIFFRAC$^{plus}$ TOPAS 4.2 software was used for this phase analysis.

3. Elemental Analysis

To ascertain the elemental composition, ICP-AES (inductively coupled plasma atomic emission spectroscopy) was carried out with the ICP Spectro Modula device. The following was used as chemicals: HF 40% pA., HCl 37% pA. The sample was finely ground. 50 mg of the sample was weighed into a 50-ml plastic tube and 2 ml hydrofluoric acid and 2 ml hydrochloric acid were added. Solubilization took place in a heating block at 85° C. until a clear solution formed. This was followed by tempering, filling up and shaking. All elements were measured using ICP: Mo: wavelength: 202.030 nm, standards: 300, 400, 500 ppm; V: wavelength: 290.882 nm, standards: 20, 50, 100 ppm; Nb: wavelength: 316.340 nm, standards: 20, 50, 100 ppm; Te: wavelength: 214.281 nm, standards: 50, 100, 150 ppm.

All standards were adjusted with HF and HCl. The evaluation followed the following calculation: w(E* in percent)=β (E*-measurement value in mg/l)×V(measuring flask in l)×100/m(initial weight in mg) (E*=respective element).

4. Thermogravimetry

The thermogravimetric analysis was carried out with the NETZSCH STA 409 PG device. As the sample's initial weight, 530.490 mg was placed in an $Al_2O_3$ crucible. Firstly the sample was pre-dried in an atmosphere of synthetic air SynLuft 80/20 with a throughflow of 100 ml/min. The temperature programme consisted of maintaining at room temperature (30° C.) for 30 min, heating to 120° C. at 5° C./min and maintaining at 120° C. for 180 min. Constant mass of the residual mass was then reached. The initial weight for the then subsequent oxidation was calculated from the residual mass. The measuring cell was pre-evacuated and flooded with pure oxygen for pre-treatment. The temperature programme consisted of maintaining at 120° C. for 30 min, heating to 500° C. at 5° C./rain and maintaining at 500° C. for 180 min, constant mass was then reached.

EXAMPLES

Two examples were carried out in which different molar ratios of vanadium, niobium, tellurium, manganese, cobalt and optionally nickel to molybdenum were used as a basis. Citric acid and ethylene glycol were additionally used as reducing agent and/or chelating agent.

Table 1 shows the combinations of components of the composition chosen and finally measured with ICP-AES in Examples 1 to 2 in respect of the molar ratio to molybdenum.

TABLE 1

|  | Mo | V | Nb | Te | Mn | Co | Ni | Citric acid | Ethylene glycol |
|---|---|---|---|---|---|---|---|---|---|
| Ex. 1 | 1 | 0.22 | 0.18 | 0.18 | 0.08 | 0.0375 | 0.02 | 0.075 | 0.075 |
| Ex. 2 | 1 | 0.22 | 0.18 | 0.18 | 0.07 | 0.0375 | 0 | 0.075 | 0.075 |

Listed in Table 2 are the corresponding quantities of the compounds of the respective metals used, which were combined for Examples 1 and 2 into the respective catalyst precursor material mixtures. Approx. 0.025 mol molybdenum was used in each example.

TABLE 2

|  | $MoO_3$ [g] | $V_2O_5$ [g] | Nb-Oxalat* [ml] | Te $(OH)_6$ [g] | Mn $(NO_3)_2$ × $4H_2O$ [g] | Ni $(NO_3)_2$ × $6H_2O$ [g] | Co $(NO_3)_2$ × $6H_2O$ [ml] | Zitronensaure [g] | Ethylene glykol [ml] | $H_2O$ [ml] |
|---|---|---|---|---|---|---|---|---|---|---|
| Bsp. 1 | 3.6 | 0.5 | 11.25 | 1.033 | 0.5020 | 0.1454 | 0.2728 | 0.3602 | 0.105 | 39 |
| Bsp. 2 | 3.6 | 0.5 | 11.25 | 1.033 | 0.4393 | 0 | 0.2728 | 0.3602 | 0.105 | 39 |

*0.4M Nb solution of $(NH_4)$ $(NbO (C_2O_4)_2(H_2O)_2)$ × $3H_2O$

Nb oxalate was provided as approx. 0.4 M Nb solution which had a total volume of 200 ml, in which 34.8 g of the Nb oxalate compound named in the table was dissolved.

The production of the catalyst materials of Examples 1 and 2 was carried out in each case as follows:

$MoO_3$, $V_2O_5$, $Te(OH)_6$, $Co(NO_3)_2 \times 6H_2O$ were mixed in the quantities named in Table 2 with a mortar in an agate mortar. $Ni(NO_3)_2 \times 6H_2O$ was additionally admixed for Example 1. Then, as described above, the 0.4 M aqueous solution of Nb oxalate was produced. Then citric acid, then $Mn(NO_3)_2 \times 4H_2O$ and ethylene glycol were added to the Nb oxalate solution. The thus-obtained solid and liquid phases were mixed in a Teflon reaction vessel and distilled water was added to same in the quantity named in Table 2. The Teflon autoclaves were then rinsed with nitrogen for approx. 2 minutes at a flow rate of 100 ml/min. A hydrothermal synthesis in a microwave oven then took place at a temperature setting of approx. 175° C. for 3 hours at a starting pressure of from 3 to 6 bar and a maximum pressure of 30 bar accompanied by stirring, wherein cruciform magnetic stirring bars were used. During the hydrothermal synthesis the temperature fluctuated between 175 and 203° C. The reaction mixture was then cooled and treated by washing three times with 50 ml distilled water. Drying was then carried out overnight at 120° C. and the obtained material was then ground in an agate mortar. Finally, the obtained reaction product was heated in the $N_2$ stream at 200° C. for 2 hours and then activated in the $N_2$ stream at 600° C. for 2 hours.

The specific surface area for the catalyst materials of Examples 1 and 2 was determined as explained above and a BET surface area of 8.8 $m^2$/g was obtained for Example 1 and of 12 $m^2$/g for Example 2 as a result.

Relative to Mo=1, the following values of the composition resulted from the associated elemental analysis by means of ICP-AES for the catalyst material of Example 1 (in respect of the molar ratio to molybdenum):

TABLE 3

| Ex. 1 | Mo | V | Nb | Te | Mn | Co | Ni |
|---|---|---|---|---|---|---|---|
| experimental | 1 | 0.231 | 0.195 | 0.196 | 0.071 | 0.035 | 0.018 |
| nominal | 1 | 0.220 | 0.180 | 0.180 | 0.080 | 0.038 | 0.020 |

This good correspondence of the experimental and nominal composition of the catalyst material obtained in Example 1 was confirmed by means of ICP-AES by an elemental analysis of the mother liquor and of the washing water, which had also contained small residues of the filter residue, which yielded the following values:

| Ex. 1 | Mother liquor | Washing water |
|---|---|---|
| Mo content | 0.088% | 0.082% |
| V content | 0.245% | 0.088% |

-continued

| Ex. 1 | Mother liquor | Washing water |
|---|---|---|
| Te content | 0.003% | 0.006% |
| Nb content | <0.002% | 0.002% |

This means that in the method for producing the catalyst material according to embodiments of the invention, a quantitative conversion of the compounds used takes place.

An oxidation of propane was carried out to evaluate the effectiveness of the catalyst materials which were obtained in Examples 1 and 2. A multichannel continuous flow reactor was used for this, and the propane to be tested was admitted evenly through its channels. The catalyst materials of Examples 1 and 2 to be tested were filled respectively into different channels. Each channel contained approx. 500 mg of the respective catalyst material. The throughflow rate was 20 ml/min/channel, which corresponds to a GHSV of 2400 $h^{-1}$. The reaction temperature was 400° C. The composition of the gas was propane:Kr:$O_2$:He:$H_2O$=3:1:6:70:20. The oxidation was carried out for approx. 6 h. The quadrupole mass spectrometer Prisma QMS 2000 from Pfeiffer Vacuum Technology was used for the product analysis.

Table 4 reproduces the conversion rates for propane achieved with the catalyst materials of Examples 1 and 2, as well as the yields and selectivity for acrylic acid.

TABLE 4

|  | Propane conversion [%] | Acrylic acid yield [%] | Acrylic acid selectivity [%] |
|---|---|---|---|
| Ex. 1 | 73 | 58 | 80 |
| Ex. 2 | 72 | 53 | 73 |

It can be seen from Table 4 that the yield of acrylic acid reached values of over 50%. Additionally, Table 4 shows that the catalyst materials of Examples 1 and 2 possessed at the same time a high selectivity for the formation of acrylic acid from propane.

Catalyst materials in which Mn and Co were not contained were produced as comparison examples 1 to 3. The production was carried out as described for Examples 1 and 2, but the V, Mn, Co, Nb, Ni, Te, citric acid and W contents were adapted such that the molar ratios to molybdenum named in the following Table 5 were obtained.

TABLE 5

| Comparison ex. | Mo | V | Mn | Co | Nb | Ni | Te | Citric acid | W |
|---|---|---|---|---|---|---|---|---|---|
| 1 | 1 | 0.26 | 0.00 | 0.00 | 0.16 | 0.00 | 0.16 | 0.12 | 0.10 |
| 2 | 1 | 0.27 | 0.00 | 0.00 | 0.18 | 0.10 | 0.17 | 0.00 | 0.00 |
| 3 | 1 | 0.27 | 0.00 | 0.00 | 0.17 | 0.10 | 0.17 | 0.04 | 0.00 |

Table 6 reproduces the conversion rates for propane obtained with comparison examples 1 to 3, as well as the associated acrylic acid yields and selectivities.

TABLE 6

| Comparison ex. | Propane conversion [%] | Acrylic acid yield [%] | Acrylic acid selectivity [%] |
|---|---|---|---|
| 1 | 55 | 38 | 70 |
| 2 | 53 | 39 | 73 |
| 3 | 66 | 48 | 72 |

Tables 4 and 6 show that a higher conversion rate for propane and a higher acrylic acid yield were achieved in the oxidation of propane to acrylic acid with the catalyst materials according to the invention in comparison with catalyst materials in which Mn and Co were not contained.

In the oxidation of hydrocarbons, the catalyst materials according to the invention thus bring about high yields and/or a high selectivity, in particular in the oxidation of propane to acrylic acid.

Figure 1:
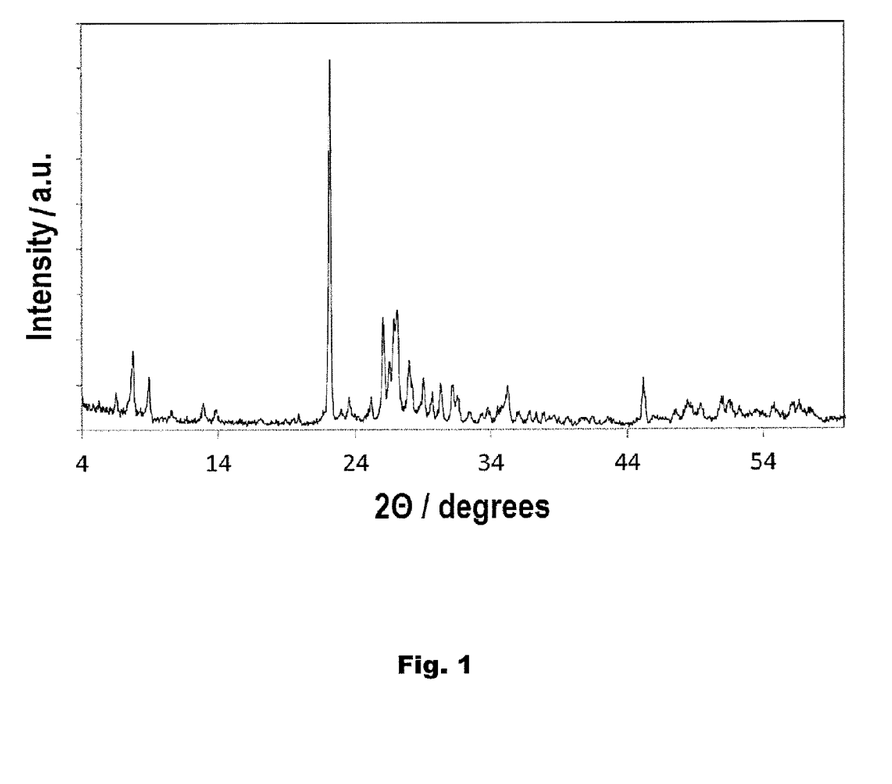
FIG. 1 is an X-ray diffractogram of Example 1.

FIG. 1 shows an XRD diffractogram of Example 1 recorded as described above. Diffraction reflexes with the following characteristic diffraction angles, or their peaks, with high intensity can be seen in the diffractogram: P1=(2θ) 6.52 with an intensity of 166 (arbitrary units (a.u.)); P2=(2θ) 7.76 (rounded to 7.8) with an intensity of 348 (a.u.); P3=(2θ) 8.96 with an intensity of 231 (a.u.). It can be concluded from these diffraction reflexes that the M1 phase is present in the sample of Example 1 in a proportion of over 70 wt.-% to up to 100 wt.-%. Further pronounced diffraction reflexes, or peaks of the associated diffraction angles, P4=(2θ) 26.04 (rounded to 26.0) with an intensity of 492 (a.u.), P5=(2θ) 27.08 (rounded to 27.1) with an intensity of 529 (a.u.), P6=(2θ) 27.96 (rounded to 28.0) with an intensity of 304 (a.u.), as well as P7=(2θ) 35.2 with an intensity of 194 (a.u.) and P8=(2θ) 48.4 with an intensity of 126 (a.u.) can also be seen. Deviations of ±0.5 may occur for the peaks of all diffraction angles. For example, the following characteristic intensity ratios result therefrom:

$R1 = P4/(P4+P5) = 0.48$ $R2 = P5/(P5+P6) = 0.64$ $R3 = P5/(P5+P2) = 0.60$

The X-ray amorphous proportion of the catalyst material of Example 1 was determined as 37%.

Figure 2:
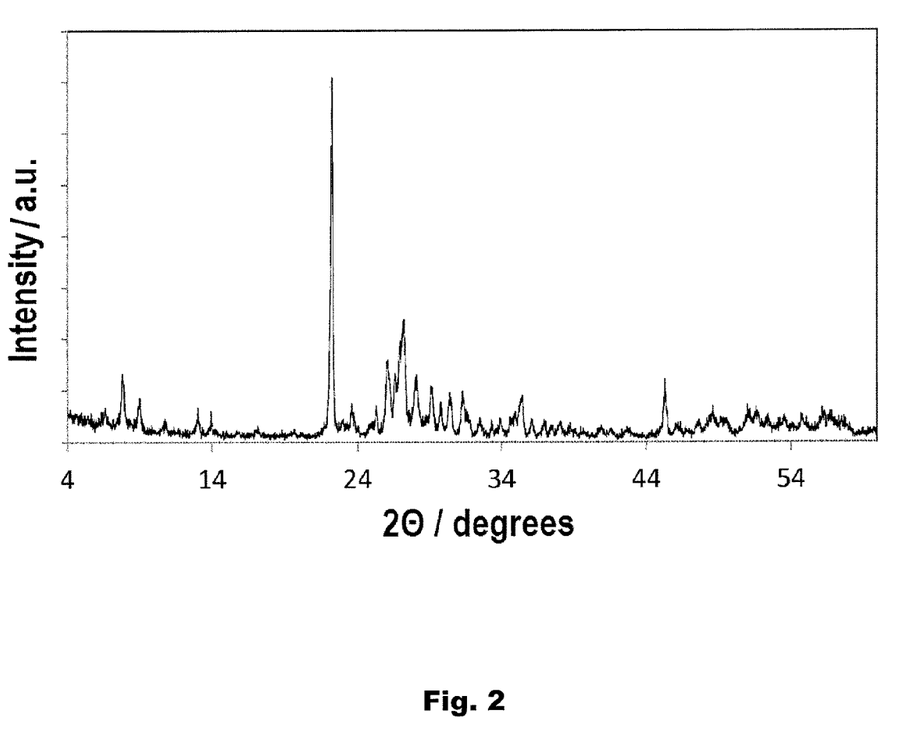
FIG. 2 is an X-ray diffractogram of Example 2.

An XRD diffractogram of Example 2 shown in FIG. 2 resulted in the following characteristic diffraction reflexes, or peaks P1 to P8 of the associated diffraction angles, with high intensity:

|  | 2θ | Int. (a.u.) |
|---|---|---|
| P1 | 6.56 | 66 |
| P2 | 7.78 | 130 |
| P3 | 8.92 | 76 |
| P4 | 26.08 | 154 |
| P5 | 27.04 | 262 |
| P6 | 27.94 | 146 |
| P7 | 35.20 | 88 |
| P8 | 48.48 | 66 |

Deviations of ±0.5 may occur for the peaks of all diffraction angles. As in Example 1, it can be concluded from diffraction reflexes P1, P2 and P3 that the M1 phase is present in the sample of Example 2 in a proportion of over 70 wt.-% to up to 100 wt.-%, in particular in a proportion greater than 99 wt.-%.

For example, the following characteristic intensity ratios result from the diffraction angles of Example 2 above:

$R1 = P4/(P4+P5) = 0.37$ $R2 = P5/(P5+P6) = 0.64$ $R3 = P5/(P5+P2) = 0.66.$

The following composition was obtained for the powder obtained in Example 2 by elemental analysis by means of ICP-AES:

|  | Reference | Actual |  |
|---|---|---|---|
| Mo | 42.76 | 42.6 | wt.-% |
| V | 5.00 | 5.5 | wt.-% |
| Te | 10.24 | 9.0 | wt.-% |
| Nb | 7.45 | 8.0 | wt.-% |
| Mn | 1.71 | 1.53 | wt.-% |
| Co | 0.98 | 0.95 | wt.-% |

The thermogravimetric oxidation of the catalyst material of Example 2 yielded an integral weight gain of approx. 0.79 wt.-%+0.12 wt.-% after heating to 500° C. for 290 min. up to the constant weight, i.e. the weight gain is approx. 0.91 wt.-% in total. A molar ratio of oxygen to metal in the sample of Example 2 of approximately 2.635 is calculated from the elemental composition given above of the metal cations obtained by analysis of Example 2 by means of ICP-AES and the ascertained weight gain, assuming the complete oxidation of all constituent metal ions. This results in a reduction rate of the catalyst material of Example 2 of approximately 2.635 from the weight gain, assuming the complete oxidation of all metal ions.

The invention claimed is:

1. A catalyst material for the oxidation and/or oxidative dehydrogenation of hydrocarbons, comprising
    a) molybdenum (Mo)
    b) vanadium (V)
    c) niobium (Nb)
    d) tellurium (Te)
    e) manganese (Mn)
    f) cobalt (Co)
    in which the respective molar ratio of the elements manganese and colbalt to molybdenum lies in the range of from 0.01 to 0.2.

2. The catalyst material according to claim 1, in which the molar ratio of at least one element, which is selected from vanadium, niobium and tellurium, to molybdenum lies in the range of from 0.1:1 to 0.3:1 or 0.13:1 to 0.27:1; and/or
    in which nickel is contained in a molar ratio to molybdenum in the range of from 0 to 0.04.

3. The catalyst material according to claim 1 with an X-ray diffractogram which has diffraction reflexes h, i, k and l the peaks of which lie at the diffraction angles (2θ) 26.0±0.5 (h), 27.1±0.5 (i), 7.8±0.5 (k) and 28.0±0.5 (l); and/or
    in which the intensities $P_h$, $P_i$, $P_k$, $P_l$ of the diffraction reflexes h, i, k and l satisfy the following equations, with $R_{x\ (x=1\ to\ 3)}$ as the intensity ratio defined by the equations:

$R_1 = P_h/(P_h + P_l) > 0.3$; and/or $R_2 = P_i/(P_i + P_l) > 0.5$; and/or $R_3 = P_i/(P_i + P_k) < 0.8$; and/or in which, in the X-ray diffractogram, the diffraction reflex i has the second highest intensity and/or the diffraction reflex h has the third highest intensity.

4. The catalyst material according to claim 1 in which the catalyst material is a catalyst precursor material.

5. The catalyst material according to claim 4, in which the catalyst precursor material contains at least one excipient, with a molar ratio of at least one of the excipients to molybdenum in the range of from 0.05:1 to 0.15:1; and/or
    in which the at least one excipient is selected from the group consisting of polyols, polyetherols, ethylene glycol, propylene glycol, glycerol, butylene glycol, citric acid, tartaric acid, malic acid, lactic acid, pyruvic acid, oxalic acid, malonic acid, glycolic acid, glyoxylic acid, gluconic acid, glucuronic acid, oxamic acid, oxaloacetic acid, tricarballylic acid, glyceric acid, tartronic acid, succinic acid, glutaric acid, sorbitol, mannitol, maleic acid, fumaric acid, nitrilotriacetic acid, or any mixture thereof.

6. The catalyst material according to claim 4, in which at least one excipient is contained with a molar ratio to molybdenum of 0.05:1, 0.075:1 or 0.1:1.

7. The catalyst material according to claim 5, in which vanadium, niobium, tellurium, cobalt, manganese, nickel, ethylene glycol and/or citric acid have the following molar ratios to molybdenum:
    V: 0.22 or 0.23
    Nb: 0.18 or 0.195
    Te: 0.18 or 0.196
    Mn: 0.07 or 0.08
    Co: 0.0375
    Ni: 0 or 0.02 and/or
    ethylene glycol: 0.075 and/or
    citric acid: 0.075.

8. The catalyst material according to claim 1, in which the catalyst material is a mixed oxide with the formula $MoV_aNb_bTe_cMn_dCo_eNi_fO_x$ and in which at least one of the following conditions applies:
    a=0.22 or 0.23
    b=0.18 or 0.195
    c=0.18 or 0.196
    d=0.07 or 0.08
    e=0.0375
    f=0 or 0.02 and
    x=2.635 or mole number which is determined by the valence and frequency of the elements other than oxygen.

9. The catalyst material according to claim 1, in which the catalyst material contains carbon; and/or
    in which the molar ratio of oxygen to metal lies in the range of from 2 to 3; and/or
    wherein the catalyst material has a reduction rate of between 2 and 3.

10. The catalyst material according to claim 1, in which the catalyst material is free of at least one element selected from Ta, In, Cu, Ce, Cr, Bi, Fe, P, Sb, Sn, Si, Ti, Zr, W, Ni, noble metals, Rh, Pd, Ag, Ir, Pt and Au.

11. The catalyst material according to claim 1, in which the catalyst material is obtained and/or activated hydrothermally and/or is pulverulent;
    and/or in which the catalyst material contains phase-pure M1 phase or substantially consists thereof;
    and/or
    in which the catalyst material contains more than 70 wt.-% M1 phase, and/or the remainder contains more than 90 wt.-% M2 phase or substantially consists of the M2 phase;
    and/or
    in which the X-ray amorphous proportion of the catalyst material is smaller than 40%; and/or
    in which the catalyst material has a specific surface area according to BET in the range of from 1 to 40 m²/g.

12. A catalyst for the oxidation and/or oxidative dehydrogenation of hydrocarbons, comprising a catalyst material according to claim 1.

13. The catalyst according to claim 12, in which the catalyst material is applied to a support.

14. A method for oxidation and/or oxidative dehydrogenation of hydrocarbons or for selective oxidation of propane to acrylic acid, comprising catalyzing at least one of said reactions with the catalyst material of claim 1.

15. A method for producing a catalyst material for the oxidation and/or oxidative dehydrogenation of hydrocarbons, comprising
    providing a catalyst precursor material according to claim 4 as aqueous mixture, and
    thermally treating the aqueous mixture at temperatures of from 100 to 250° C. for at least 1 hour, and/or at 3 to 35 bar.

16. The method according to claim 15, comprising
    activating the thermally treated mixture in an inert gas atmosphere at 500 to 700° C. for at least 1 hour.

17. The method according to claim 16, in which the thermal treatment is carried out at 200° C. for 2 hours and/or in which the activation is carried out at 600° C. for 2 hours.

18. A catalyst material, obtainable or obtained by the method according to claim 15.

19. A method for the selective oxidation of propane to acrylic acid in the presence of oxygen and a catalyst according to claim 12.

* * * * *